(12) United States Patent
Zhou et al.

(10) Patent No.: US 9,943,627 B2
(45) Date of Patent: Apr. 17, 2018

(54) METHOD OF PRODUCING PERSONALIZED BIOMIMETIC DRUG-ELUTING CORONARY STENTS BY 3D-PRINTING

(71) Applicants: Yujie Zhou, Beijing (CN); Wei Sun, Beijing (CN); Qian Ma, Beijing (CN); Lei Zhang, Beijing (CN)

(72) Inventors: Yujie Zhou, Beijing (CN); Wei Sun, Beijing (CN); Qian Ma, Beijing (CN); Lei Zhang, Beijing (CN)

( * ) Notice: Subject to any disclaimer, the term of this patent is extended or adjusted under 35 U.S.C. 154(b) by 236 days.

(21) Appl. No.: 14/743,782

(22) Filed: Jun. 18, 2015

(65) Prior Publication Data

US 2016/0256610 A1 Sep. 8, 2016

(30) Foreign Application Priority Data

Mar. 3, 2015 (CN) ................. 2015 1 0093769
Apr. 28, 2015 (CN) ................. 2015 1 0204358

(51) Int. Cl.
| | | |
|---|---|---|
| *A61L 31/16* | (2006.01) | |
| *A61F 2/82* | (2013.01) | |
| *A61L 31/10* | (2006.01) | |
| *A61L 31/14* | (2006.01) | |
| *B33Y 80/00* | (2015.01) | |
| *B33Y 70/00* | (2015.01) | |
| *A61L 31/06* | (2006.01) | |
| *A61B 90/00* | (2016.01) | |
| *B29C 64/106* | (2017.01) | |
| *B29C 64/153* | (2017.01) | |
| *B33Y 10/00* | (2015.01) | |
| *B33Y 30/00* | (2015.01) | |
| *B33Y 50/02* | (2015.01) | |
| *B29K 67/00* | (2006.01) | |

(52) U.S. Cl.
CPC .............. *A61L 31/16* (2013.01); *A61B 90/06* (2016.02); *A61F 2/82* (2013.01); *A61L 31/06* (2013.01); *A61L 31/10* (2013.01); *A61L 31/148* (2013.01); *B29C 64/106* (2017.08); *B29C 64/153* (2017.08); *B33Y 70/00* (2014.12); *B33Y 80/00* (2014.12); *A61B 2090/061* (2016.02); *A61F 2210/0004* (2013.01); *A61F 2230/0067* (2013.01); *A61F 2230/0069* (2013.01); *A61F 2240/001* (2013.01); *A61F 2240/002* (2013.01); *A61F 2250/0067* (2013.01); *A61L 2300/416* (2013.01); *A61L 2420/06* (2013.01); *B29K 2067/046* (2013.01); *B33Y 10/00* (2014.12); *B33Y 30/00* (2014.12); *B33Y 50/02* (2014.12)

(58) Field of Classification Search
CPC ............ B29C 67/0055; B29C 67/0077; B29C 64/106; B29C 64/153
USPC .................................. 264/308, 408, 482, 497
See application file for complete search history.

(56) References Cited

U.S. PATENT DOCUMENTS

| | | | |
|---|---|---|---|
| 6,730,252 B1 * | 5/2004 | Teoh ........................ | A61L 27/18 264/178 F |
| 2008/0221439 A1 * | 9/2008 | Iddan ...................... | A61B 6/5217 600/424 |
| 2014/0088698 A1 * | 3/2014 | Roels ....................... | G06T 19/20 623/2.38 |

FOREIGN PATENT DOCUMENTS

CN 104224412 A 12/2014

* cited by examiner

*Primary Examiner* — Leo B Tentoni
(74) *Attorney, Agent, or Firm* — Oliff PLC

(57) ABSTRACT

A method for using 3D printing technology produces personalized biomimetic drug-eluting coronary stent and the product thereof. The process of manufacturing stent, based on coronary angiography imaging data, measures the diameter of diseased coronary and conducts 3D reconstruction. A personalized stent for each patient according to diameter, length, and morphological characteristics of target vessel that suited to the lesion is produced. The coronary stent is formed from biodegradable poly-L-lactic acid (PLLA) or other materials. The stent is modeled by 3D printing and then coated with polymers carrying antiproliferative drug to reduce restenosis (the polymers is a mixture of antiproliferative drug and PDLLA at a ratio of 1:1). The biomimetic drug-eluting coronary stent produced by 3D printing technology is personalized stent for each patient according to different characteristics of diseased coronary, reduces the incidence of vascular injury, thrombosis, dissection and other complications caused by stent and vessel diameter mismatch.

4 Claims, 1 Drawing Sheet

US 9,943,627 B2

METHOD OF PRODUCING PERSONALIZED BIOMIMETIC DRUG-ELUTING CORONARY STENTS BY 3D-PRINTING

TECHNICAL FIELD

This invention belongs to the technical field of medical equipment, specifically belongs to a method of producing personalized biomimetic drug-eluting coronary stents produced by 3D-printing and the product thereof.

BACKGROUND 3D-printing (also known as 3D-rapid prototyping or additive material manufacturing) is a new manufacturing technology raised from the late 1980s. It is a kind of new digital molding technology. Three-dimensional objects may be produced rapidly by analysing some data such as computer aided design (CAD) model or computed tomography (CT) data and using accurate 3D-deposition under the control of computer. These objects can be of almost any shape or geometry, and are applied in many technical fields.

3D-printing is a revolutionary manufacturing technique based on the technical principle of printers and then manufactures layer by layer. It can be referred as 'Additional material manufacturing technology' while the traditional productive technique is referred as 'Reductive material manufacturing technology'. It's featured as cost-effective, personalized and with short production cycles. The components produced by 3D-printing for airplanes, space shuffles and fusion projects are lighter, firmer and cheaper compared with regular ones, even without any waste. Thus 3D-printing has been renowned as "the most remarkable tool for the $3^{rd}$ industrial revolution".

In recent years, much attention is paid to research and develop 3D-printing to produce biomedical polymer material. The advantage of 3D-printing is that products can be designed according to each patient's specific condition with flexible design. In medical and health industry, personalized biomedical polymer material suitable for each patient is produced rapidly and accurately by 3D-printing. Meanwhile, the micro structure of the material is also controlled precisely. Therefore, the new technique of producing medical polymer material is undoubtedly promising when applying to biomedicine.

Coronary artery disease has endangered people's life in modern society, is one of common cardiovascular diseases. It's featured with high rate of prevalence, mortality, readmission and complications. For treating cardiovascular diseases, the treatment of coronary artery diseases is very important, and coronary intervention has become the primary method to treat coronary artery disease. So far, the development of coronary intervention involves 3 stages: percutenous transluminal coronary angioplasty, implanting bare-metal stents and implanting drug-eluting stents. Although the metal composition of stent body, polymer carrier and antiproliferative drug are improved a lot, two dilemmas remain unsolved: the metal material of stent and its cylindrical structure. The problems are as follows:

(1) The permanent existence of metallic stents could bring complications like late in-stent thrombosis, chronic inflammation, restenosis and stent fracture. Meanwhile, patients have to take lifelong anti-platelet drugs which would increase bleeding risk. (2) The diameter of coronary artery is gradually smaller and sometimes the gap of diameters between proximal and distal segments of culprit arteries could be remarkable which make the lumen of vessels sharply tapered. These days, traditional cylindrical stents are cylinder, may not suitable to these cone-shaped arteries with neither single stent nor two stents techniques: when implanting one stent may not expand efficiently caused by mismatch of stent diameter and vessel diameter thus lead to in-stent thrombosis, incomplete stent apposition, coronary dissection or in-stent restenosis. When implanting two stents, on the other hand, could increase the risk of restenosis and thrombosis due to overlapping area between stents, the total expense is raised. Additionally, traditional cylindrical stent couldn't match the hetero-morphic coronary artery such as aneurysm.

Aimed at above problems caused by metal material of stent body, the emergence of biodegradable stents emerged and marked the 4th revolution of coronary intervention. With regard to the conical/abnormal coronary artery, Biodegradable coronary stents suitable for the morphological characteristics of each patient are approved to have enormous Scientific, Economic and Social values.

Chinese patent CN104224412A discloses a method for producing coronary artery stent with 3D printing technology. By controlling 3D printing program, the mixture of stainless steel powder or nickel titanium powder with stearic acid powder are combined with adhesive to form the stent prototype, then after degreasing, sintering and cooling, eventually the coronary artery stent is generated. It uses metallic materials with 3D-printing technology to produce cylindrical stent, but it did not take the advantage of 3D-printing in customization, and not used the most advanced biodegradable materials, so it is failed to solve the problem of conical/abnormal vessel stenosis and failed to avoid the disadvantage of conventional stent. Unfortunately, it did not show great value in clinical practice.

DISCLOSURE OF THE INVENTION

The technical problem to be solved is to overcome the shortage of conventional stent which is it can't completely relieve the stenosis of conical/abnormal vessel, thus providing a method using 3D printing technology to produce a personalized biomimetic drug-eluting coronary stent.

The present invention also provides a personalized biomimetic drug-eluting coronary stent produced by 3D printing technology, the stent produced on the basis of patients' vascular morphology will have better effect on relieving cylindrical, conical or abnormity vascular stenosis.

This invention provides a method using 3D printing technology to produce biomimetic drug-eluting coronary stent, comprising the steps of:

(1) according to coronary angiography, measuring the diameter of diseased coronary artery by quantified coronary angiography (QCA), and designing the coronary stent suitable for the patient by 3-dimensional reconstruction;

(2) utilizing Fused Deposition Modeling/Manufacturing (FDM), Melted Extrusion Modeling (MEM), Selective Laser Sintering (SLS), Selective Laser Melting (SLM) or other Addictive Manufacturing technique to create 3D-printing platform;

(3) on 3D-printing platform of coronary stent, melt extrusion nozzles, jet nozzles, SLS or SLM are to be used to manage biodegradable materials. High-energy beam selected melting or sintering material, or other materials, controlling with hierarchical algorithm and molding control software to produce the biodegradable drug-eluting coronary stents.

Preferably, in step (3), when the printing process bases on FDM/MEM or a similar technique, the melted extrusion nozzle could be air operated nozzle, screw nozzle, or nozzles that using feeding polymer wire as driving force, and the diameter of the filament extruded by the nozzle could be 50-300 μm; when the addictive manufacturing technic is based on using High Energy Beam, the beam could be laser or High-power white light, feature sizes of the single selected melting or single selected sintering could be 50-300 m.

Preferably, in step (3), the biodegradable material is PLLA.

The present invention also provides a coronary stent produced by above method of manufacturing biomimetic drug-eluting coronary stent by 3D printing technology.

Furthermore, the stent is cylindrical, conical or abnormity shaped. Preferably, the surface of stent is coated with polymer carrying antiproliferative drug.

The antiproliferative drug and PDLLA mixed at a ratio of 1:1 in quality.

This invention provides a method of using 3D printing technology to produce personalized biomimetic drug-eluting coronary stent, the stent produced by this method on the basis of patients' vascular morphology will have better effect on relieving cylindrical, conical or abnormity shaped vascular stenosis. The personalized biomimetic drug-eluting coronary will reduce the incidence of incomplete stent apposition or sandwish, thrombosis, dissection, myocardial infarction or other complications caused by mismatch of stent diameter and vessel diameter. It is expected to save more lives of patients.

The biodegradable materials in biomimetic drug-eluting coronary stent produced by 3D printing technology are the same with that of conventional stent which made by PLLA material in hollow structure. The only difference is that the former can personalize according to the vessel of patient.

Also, the stent can be made in other materials with 3D printing technology according to the situation, in order to improve clinical efficacy.

The 3D printing technology according to the invention is based on 3D printing equipment of the melt-extrusion process or injection/deposition technology of other material. As a printing platform of coronary stents, the 3D printing technology used clinically promotes the process of the personalized coronary artery intervention therapy. It has considerable scientific, economic and social value.

(1) Scientific value: The development of biomimetic conical biodegradable coronary stent is geared to the needs of many patients, in line with the trend of individualized treatment. It also can make up for the lack caused by the mismatch shape between bracket and the blood vessels to a great extent, avoid long-term impact to coronary due to the metal stents. It is expected to reduce the complications of coronary artery disease intervention therapy, revascularization rate and mortality, improve prognosis and the quality of life of patients.

(2) Economic value: Traditional manufacturing techniques are 'Reductive material manufacturing technology". It needs to manufacture coronary stent based on manufacturing molds, which are produced in advance. Therefore, the traditional manufacturing techniques are only suitable for mass production of the same model and are not suitable for personalized needs due to the high cost. In this regard, the new 3D printing technology stent has unique advantages. 3D printing is 'additional material manufacturing technology', it does not require mold manufacturing, only through measuring the diameter of diseased coronary artery by coronary angiography and designing the personalized coronary stent by software design, a personalized coronary stent can be printed out. This technology has many advantages such as low manufacturing costs, short production cycle, and can best meet the individual needs. There are many advantages such as low cost, short production cycle and satisfying the personalized need. Therefore, a new type of coronary stent is expected to get stronger, cheaper, and even "zero waste" of raw material through produced by 3D printing technology.

(3) Social values: The design concept of coronary stent in present invention is put forward in the world for this first time, with original innovation significance. This invention plays a key role in promoting the development of the personalized coronary intervention treatment and will possibly leading the fifth worldwide coronary intervention revolution.

DETAILED DESCRIPTION

In order to make the purpose, technical solutions and advantages of this invention clearer, this invention will be described in detail combined with the embodiments and figures below.

In clinical situation, the position and shape of the lesion in coronary artery are always different. The diameter between the proximal and the distal of the lesion sometimes has huge difference, especially on the terminal of the left main coronary artery or the ostial of the left anterior descending and the left circumflex coronary artery. Current data has shown that conical coronary artery is very common in clinic.

Figure 1:
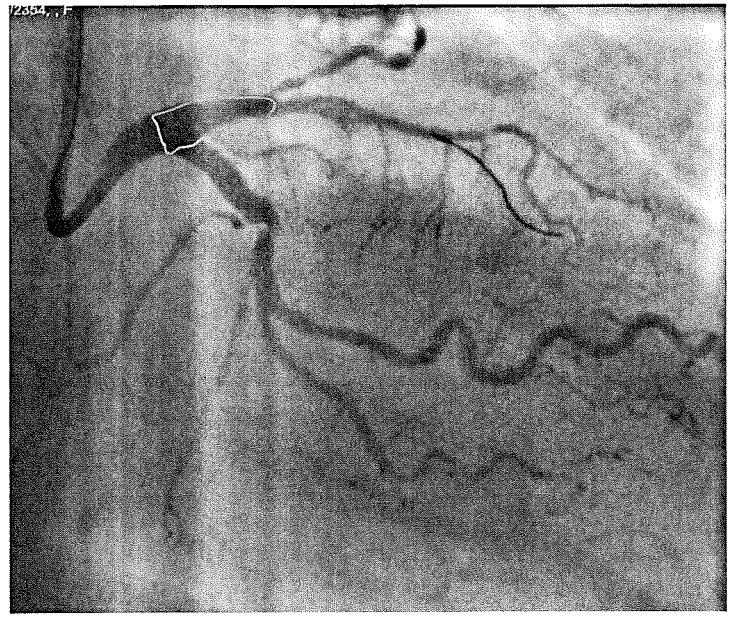
FIG. 1: Coronary angiography of the morphology of conical coronary described in embodiment.

FIG. 1 has shown an angiography of the conical coronary artery lesion. The patient has a diffuse lesion from the left main to the anterior descending coronary artery. The diameter of the left main coronary artery is 4.5 cm while it is only 2.0 cm in the anterior descending coronary artery.

Traditional coronary artery stent is cylindrical metal stent which has the same lumen diameter on both ends. When implanting this stent into the conical coronary artery, it may cause stent malapposition, dissection or in-stent thrombosis, and even serious complications such as myocardial infarction. In clinic, some vascular morphology is neither cylindrical nor conical due to aneurysm or other situations, which are not suitable for implanting the traditional cylindrical stent either. Thus, when facing conical even abnormal coronary artery, the traditional cylindrical stent can't be satisfied in clinic.

Figure 2:
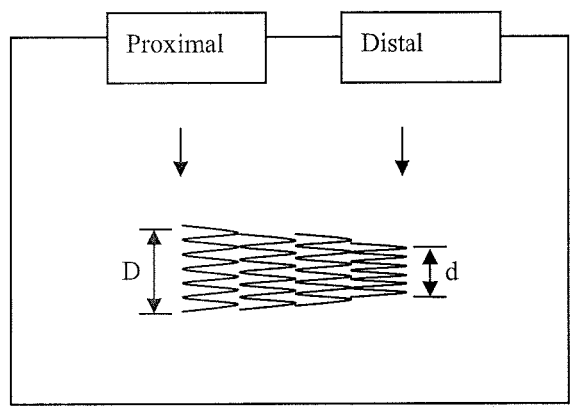
FIG. 2: The structure of conical coronary stent which suits for the conical coronary symptom, produced by 3D printing process.

FIG. 2 has shown the structure schematic of the coronary artery stent which is designed referring to the morphology of coronary in FIG. 1 and suitable for use thereof. The stent is conical structure. In the figure, the left of the stent is the distal end whose diameter is 2.0 cm, and the right of it is the proximal end whose diameter is 4.5 cm. Using the conical stent can make better adherence of both ends of the target lesion. Meanwhile, it can also avoid leading vascular dissection or rupture caused by large diameter of the distal end of the stent. Therefore, such stent structure is more suitable for the shape of lesions shown in FIG. 1.

This invention adopts 3D printing technology to produce the Personalized Biomimetic Drug-eluting Coronary Stent which was shown in FIG. 2. And the concrete steps include:

According to the coronary angiography of patients, the morphological data will be obtained by using QCA technology. After this procedure, the Personalized Biomimetic Drug-eluting Coronary Stent will be designed as the following steps. According to the inner diameter of the vascular, we can design the overall shape of the opening stent is designed, and the specific design configuration, the topology structure and details of the vascular stent is determined, then 3D data of the stent is generated. The model is dealt with the hierarchical software to generate the hierarchical data which is available in the 3D printing platform.

Based on the Fused Deposition Modeling/Manufacturing (FDM), Melted Extrusion Modeling (MEM), we choose PLLA material which has filiform (the diameter is 1.2 mm-3 mm) or nubbly shape. The material is squeezed out by using the nozzle of the melting process such as the friction drive nozzle, the screw nozzle, the pneumatic nozzle and the pointed straight write nozzle. The typical diameter of the filament extruded by the nozzle is 50-300 um, and it can be adjusted according to the performance requirement of the stent by using conventional methods in our field. 3D printing platform can complete the whole 3D printing process of the stent under the control of the software. We can also choose SLM or SLS as the forming process of 3D printing. First of all, the PLLA material is prepared into powder whose diameter range from 20 um to 150 um. Then, using the SLS or SLM printing platform to form a thin layer of the powder (the thickness is 0.05 mm-0.2 mm). After that, the laser can scan the powder layer according to each section data by the control of the special software. In the laser scanning area, powder particles have been soften or melt and adhered into form, while others which haven't been scanned can be used as a support. When completing one layer, the workbench will drop the height of a layer which has been set before to continue powdering and scanning until finishing the process of the whole stent.

After printing the stent through the 3D printing technology, the anti-proliferative drug (such as everolimus) may be coated on the surface of the stent by the traditional technology, which can make the stent's surface carry the anti-proliferative drug polymer (the polymer includes drug and PDLLA mixed by 1:1). Therefore, conical or abnormity shaped coronary artery lesion can be better solved by using the personalized biomimetic drug-eluting coronary stent produce by this invention.

Using the method of producing biomimetic stent via 3D printing technology in our invention, the most proper structure of the stent can be designed according to the structure and status of patient's lesions. It also means that any structure of the stent can be printed by only adjusting its parameters according to the common knowledge of the person skilled in this technical field if using the method in this invention.

The embodiment listed above has described further in detail for the purpose, the technical scheme and the beneficial effect of this invention. What is said above is only embodiment of this invention, which doesn't limit the scope of this invention. Any modification, equivalent replacement or improvement should be included in the scope of protection of our invention patent if it is involved in the spirit and principles of this invention.

The invention claimed is:

1. A method of producing a personalized biomimetic drug-eluting coronary stents by 3D-printing, comprising the steps of:
   (1) obtaining morphological data of a diseased coronary artery by using Quantified Coronary Angiography (QCA); designing an overall shape of a coronary stent in an expanded state, and determining topological structure of the coronary stent, thereby generating a 3D model of the coronary stent; processing a 3D model by using a layering software, so as to generate layer data for a 3D printing platform;
   wherein, the coronary stent has an overall conical shape in the expanded state, a diameter of a proximal end of the coronary stent is larger than a diameter of a distal end of the coronary stent; or, the coronary stent has an overall irregular shape in the expanded state;
   (2) performing 3D printing by means of Melted Extrusion Modeling (MEM), wherein, biodegradable material is extruded under a controlled condition through a friction drive nozzle, a screw nozzle, a pneumatic nozzle or a straight pointed nozzle, and the extruded material is manipulated by a control software of the 3D printing platform to form the coronary stent;
   or,
   performing 3D printing by means of Selective Laser Melting/Sintering (SLM/SLS), wherein, powder of biodegradable material is prepared and laid on a support plate of the 3D printing platform, and the powder is selectively scanned with controlled laser beam in a layer-by-layer manner according to said layer data;
   (3) coating the coronary stent with anti-proliferative drug, so as to produce the biomimetic drug-eluting coronary stent.

2. The method of claim 1, wherein,
   when the 3D printing is performed by means of Melted Extrusion Modeling, the extruded material has a diameter of 50-300 μm;
   or,
   when the 3D printing is performed by means of Selective Laser Melting/Sintering, the controlled laser beam has a feature size of 50-300 μm.

3. The method of claim 1, wherein, the biodegradable material is PLLA (poly-L-lactic acid).

4. The method of claim 2, wherein, the biodegradable material is PLLA (poly-L-lactic acid).

* * * * *